(12) United States Patent
Viscomi

(10) Patent No.: US 8,057,231 B2
(45) Date of Patent: Nov. 15, 2011

(54) DIRECT PRESS ON VENEER

(76) Inventor: Brian D. Viscomi, Easton, PA (US)

(*) Notice: Subject to any disclaimer, the term of this patent is extended or adjusted under 35 U.S.C. 154(b) by 69 days.

(21) Appl. No.: 11/986,636

(22) Filed: Nov. 24, 2007

(65) Prior Publication Data
US 2008/0131845 A1 Jun. 5, 2008

Related U.S. Application Data (60) Provisional application No. 60/872,464, filed on Dec. 2, 2006.

(51) Int. Cl.
*A61C 5/00* (2006.01)

(52) U.S. Cl. .................... 433/215; 433/202.1

(58) Field of Classification Search ........... 433/201.1, 433/212.1, 215, 221.1, 202.1
See application file for complete search history.

(56) References Cited

U.S. PATENT DOCUMENTS

| | | | | |
|---|---|---|---|---|
| 5,015,180 | A | * | 5/1991 | Randklev ................... 433/9 |
| 5,482,464 | A | * | 1/1996 | Shimosawa et al. ....... 433/202.1 |
| 7,393,882 | B2 | * | 7/2008 | Wu et al. ................... 523/116 |
| 7,597,556 | B1 | * | 10/2009 | Harrison, III ............... 433/89 |
| 2005/0241962 | A1 | * | 11/2005 | Tuneberg ................. 206/63.5 |

* cited by examiner

*Primary Examiner* — Cris L Rodriguez
*Assistant Examiner* — Eric Rosen
(74) *Attorney, Agent, or Firm* — Ann M. Knab (57) ABSTRACT

A direct resin veneer (2) for creating a veneer on a tooth surface comprising a thin planar expanse of an uncured restorative material, or direct resin veneer (4). The veneer (4) has a generally tooth configuration that is generously sized to permit adequate coverage for any tooth. Adhered to at least one side of the restorative material is a flexible pliant non-sticky planar sheath (6). The sheath (6) material has a curved gingival arch contour (10) for gum line alignment and various tab-like protrusions that permit placement upon a tooth. An inferior peeling tab (12) allows for sheath to be separated from the resin veneer (4) subsequent to tooth surface placement. And the lateral grasping tabs (16) permit delivery to a tooth's surface.

7 Claims, 10 Drawing Sheets

DIRECT PRESS ON VENEER

CROSS REFERENCE TO RELATED APPLICATIONS

THIS APPLICATION CLAIMS THE BENEFIT OF PROVISIONAL PATENT APPLICATION SER. NO. 60/872,464, FILED DEC. 2, 2006, BY THE PRESENT INVENTOR

FEDERALLY SPONSORED RESEARCH

Not Applicable

SEQUENCE LISTING OR PROGRAM

Not Applicable

BACKGROUND

1. Field of Invention

This document applies to the field of Dentistry and in particular to veneer the outer or facial surface of a tooth with a preformed uncured composite resin of uniform thickness for the purpose of attaining the desired esthetic result more expediently.

2. Prior Art

Many times in Dentistry, a patient will present with teeth that he or she will consider esthetically unpleasing. Typically these are the visible or front teeth that may display multiple restored areas, discolorations, uneven edges, congenital malformations, etc.

Dentists possess many restorative modalities to confront these various situations. They range from simply bleaching the teeth to fully covering the tooth with a crown. More often than not, the teeth are otherwise structurally sound and functional as to not need aggressive restoring. For these instances, dentists will elect to alter the facial or external surface of the tooth resulting in a cosmetic improvement to the tooth with minimal invasion or removal of sound tooth structure. Presently, minimally invasive cosmetic alterations of the tooth can be accomplished by placing a cover or veneer on the surface of the tooth which allows for altering both its shade and shape. This can be accomplished either with a directly applied veneer, or an indirectly applied veneer. Briefly, an indirect veneer is one that is fashioned extra-orally, typically in a dental laboratory. After tooth preparation, an impression is taken of the tooth and sent to the laboratory. The patient then returns for a subsequent visit to have the fabricated veneer inserted. The other method, direct placement, and the one that concerns this patent, is fabricated directly on the patient's prepared tooth, while the patient remains in the dental chair. The dentist, in his armamentarium, possesses an array of composite resin restorative materials of various shades with which to apply to the tooth for the purpose of shade and or anatomical alteration of the prepared tooth. Typically, the dentist will dispense the appropriate shade and quantity of resin, and apply the dispensed mass directly to the prepared tooth and proceed to tamp down the mass to a uniform thickness while simultaneously manipulating the mass to conform to the outline of the prepared tooth. The process of arriving at a uniform deposition of resin material involves the repeated application and reduction or resin before uniformity is achieved. This translates into a tedious process, consuming chair time, which can lead patient stress and a reduction of the dentist's office efficiency. DIRECT PRESS ON VENEER, by virtue of providing the clinician with a pre-shaped tooth covering consisting of uncured resin of proper shade, enables him or her in a singular motion to cover or veneer the tooth and thereby eliminate the tedium associated with the previously described conventional method of application.

Thusly, the veneer may upon application, be polymerized trimmed, polished and permanently bonded to the prepared tooth. Typically veneer resins are less viscous so that they may be manipulated more readily on the tooth surface. This lower viscosity is a result of lower filler content relative to the binding matrix. Consequently, the surface hardness is lessened and the ability to maintain a luster is diminished. The Direct Press On Veneer technique allows for a resin with higher filler content, and concomitant increased hardness and maintenance of surface luster. As an alternative, the Direct Press On Veneer may be utilized as a means for temporization when the intent of the dentist is to restore the tooth with a direct type veneer. In such case, the Direct Press On Veneer would be temporarily affixed to the prepared tooth for the purpose of intentional removal at the time of insertion of the finished direct veneer. Simultaneous application of resin to two or more teeth may provide a broader esthetic result and or serve to splint or connect teeth for the purpose of reinforcing a periodontally compromised tooth.

While there does exist a myriad of composite resin dental restorative materials, they exist primarily encapsulated in bulk form, whether it be in compule or syringe. The Direct Press On Veneer exists as a preformed entity of specific dimensions whose application is unique from the traditional manner of veneering a tooth. As such, there is no past or current modality which employs preformed, shaped, tooth facial coverings to be applied in the un-polymerized state.

Accordingly several advantages of the present provisional patent application of Brian D. Viscomi for DIRECT PRESS ON VENEER are:

1. Allows dentist to select veneer of desired shade
2. Veneer's uniform thinness eliminates bulky appearance
3. Uniform thickness allows for consistent appearance with multiple placements
4. Preformed shape is quickly adapted to tooth thereby expediting the procedure
5. Preformed veneers can serve as temporization for subsequent indirect veneer placement
6. Can be finished and polished either intra or extra-orally
7. Tint and opaque mediums may be applied to either tooth substrate or preformed veneer
8. Broad application of resin permits simultaneous multiple restorations
9. Engaging adjacent teeth may aid in splinting of a periodontally involved tooth
10. Accommodates a higher filled resin to enhance durability.

SUMMARY OF THE INVENTION

It is thus the object of this invention to provide the restorative dentist a pre-shaped, uniformly thin, uncured resin veneer for restorative purposes.

Also this invention may have periodontal considerations as a means to provide for the splinting of teeth.

It is a further aim of this invention to allow this restorative process to serve as a permanent restoration.

In addition, this invention may serve as in intermediate restoration when an indirect restoration is to be the permanent placement.

Accordingly, a pre-shaped, uniformly thin, uncured resin, which is available in multiple shade variations to serve as a permanent or temporary covering or veneer of the outer surface of a tooth to enhance its appearance and or performance.

DRAWINGS, FIGURES

FIG. 2 shows the enveloping sheath halves opened to expose the uncured composite resin veneer.

DRAWINGS REFERENCES

2. Direct Press On Veneer
4. Resin Veneer
6. Planar Sheath
8. Second Planar Sheath
10. Gingival arch contour
12. Inferior peeling tab
14. Peeling tab separator
16. Lateral grasping tab
18. operator
20. Tooth surface
22. Compressible applicator
24. Applicator body
26. Foam applicator
28. Compressive forces
30. Sliding compressive forces
32. Card applied press on veneers
34. Veneer card
36. Instrument engagement pocket
38. Engaging instrument
40. Multiply connected veneer
42. Accordion connector
44. Accordion peel strip

DETAILED DESCRIPTION

Figure 1:
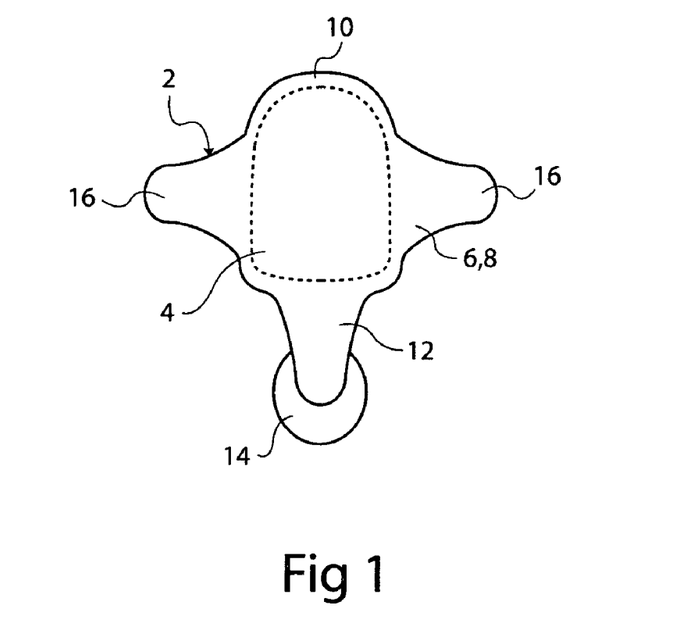
FIGS. 1 to 2 show various aspects of a preferred embodiment for the direct press on veneer.
Figure 2:
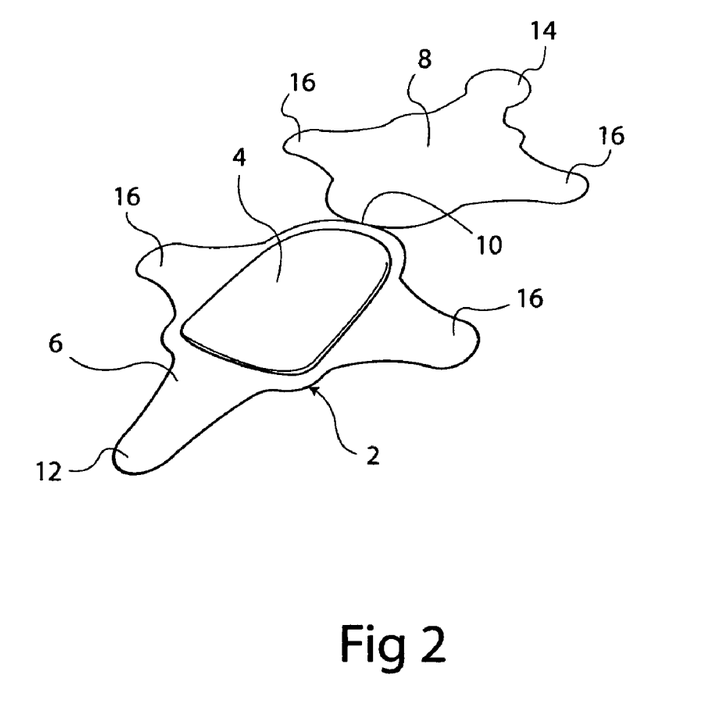

FIGS. 1A and 1B—Preferred Embodiment

A preferred embodiment of the direct press on veneer 2 of present is illustrated in FIG. 1 and FIG. 2. FIG. 1 shows a frontal orthographical view of the Direct Press On Veneer 2. The press on veneer 2 is mostly planar in dimension and is comprised of a flattened layer of composite resin. This flattened layer or resin veneer 4 is encased between two flat flexible layers, sheets or a planar sheath 6 and a second planar sheath 8. FIG. 2 shows the press on veneer 2 with the planar sheath 6 and the second planar sheath 8 separated to expose the resin veneer 4.

The resin veneer 4 is a very thin sheet of uncured composite resin and is sized to correlate with the general dimensions of a tooth's surface. Superiorly, it has a rounded portion that correlates with the gingival aspect of a tooth's surface. Laterally and medially, the veneer 4 dimensionally correlates with the buccal and lingual aspects of anterior anatomy, while the inferior portion correlates with the incisal portion of the tooth. The resin veneer's 4 surface area can vary to any dimension that desirably accommodates the anatomical variances found in patients. Furthermore, the veneer 4 is desirably thick, to ensure adequate cosmetic coverage and optimal workability while minimizing excess bulkiness.

The enveloping planar sheath 6, and second planar sheath 8 function as encasing covers, and are composed of a highly flexible, pliant material that readily adapts during a veneers 4 adaptation to a tooth surface. Furthermore, the sheaths 6, 8 are desirably non-sticky to facilitate a non disruptive separation from the encased resin veneer 4. Both sheaths 6, 8 have slightly larger dimensions relative to the resin veneer 4 to ensure total envelopment. This serves to enhance the veneer's 4 preservation and additionally to prevent contamination during pre-operative handling.

The superior aspect of the sheaths 6, 8 have curved or arched portions. These arched protrusions or gingival arch contours 10 are designed to correlate with the curved superior aspect of the resin veneer 4. Furthermore, the arch contours 10, anatomically correlate with a tooth's gum line. When placed on a tooth, the gingival arch 10 is intended to tangentially align with the gum line. The tangential alignment positions the veneer 4 a short distance below the gum line. This ensures against excessive intrusion of the resin veneer 4 into the gum area during operative adaptation to tooth surfaces.

Figure 8:
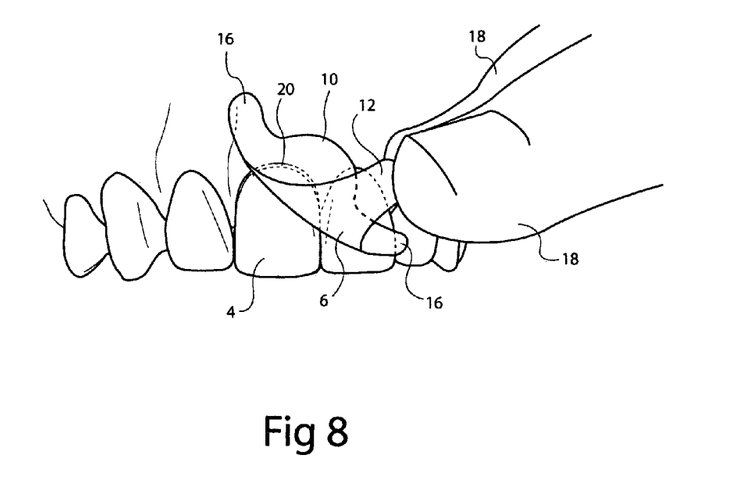
FIG. 8 shows an operator peeling the sheath away from an adapted resin veneer.

Located on the inferior aspect of the sheaths 6, 8 are elongated extensions, protrusions or inferior peeling tabs 12. The inferior peeling tabs 12 are ergonomically shaped to facilitate sheath 6, 8 separation to expose the veneer 4 (FIG. 3) Secondarily, the peeling tabs 12 function to allow sheath separation from an operatively adapted resin veneer 4 (FIG. 8).

Figure 4:
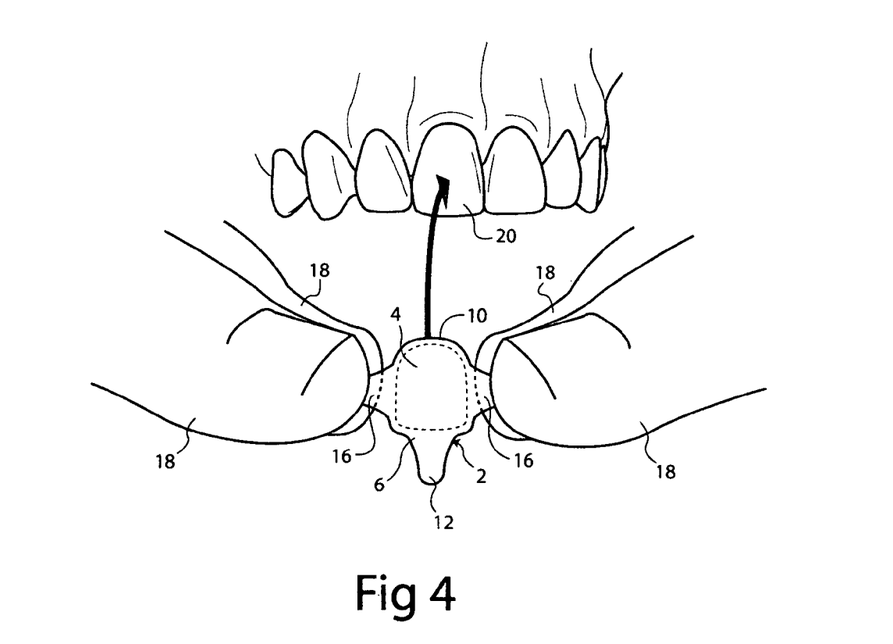
FIG. 4 shows lateral grasping tabs being gripped to aid placement on a tooth's surface.

Extending from the lateral aspects of the sheaths 6, 8 are two protrusions similar in dimension to the inferior peeling tab 12. These extensions or lateral grasping tabs 16 are intended to aid veneer deliver and placement onto a tooth by allowing a operator to grasp them (FIG. 4).

Of note, the second planar sheath 8 has a mostly identical relationship to the planar sheath 6 except for the addition of an enlarged expanse originating on the inferior peeling tab 12. The expanse or tab separator 14 is intended to desirably overlap the planar sheath's inferior peeling tab. The overlap differential aids in sheath 6, 8 separation.

The Direct Resin Veneer 2 can be manufactured by a number of mechanical means. For example, the uncured resin veneer 4 may be rolled or flattened stamped or molded into configuration and subsequently encased in between strips of sheath 6, 8 material. The sheaths 6, 8 may then be die stamped or cut into configuration. The Press On Veneer 2 may also be manufactured by placing an amount of resin between strips of sheath 6, 8 and pressing or rolling the encased resin veneer 4. Final configuration may then be achieved by stamping, cutting, pressing or laser cutting the sheath's 6, 8 into configuration.

In the preferred embodiment, the sheaths 6, 8 are composed of a non-sticky plastic pliant material. The material may be coated with Teflon or any other appropriate non-sticky emulsion that sufficiently minimizes adherence to composite resins. The sheaths 6, 8 are sufficiently stick resistant to allow for non-disruptive separation from the resin veneer 4 upon tooth application.

FIGS. 7-16 Alternative Embodiments

Figure 12A:
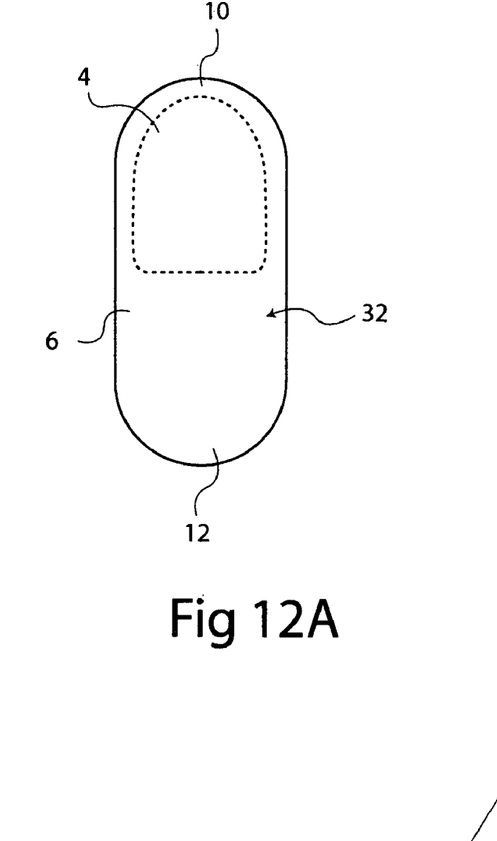
FIGS. 12 to 12B show multiple single-sided sheath Press On Veneers adhered to a card.
Figure 12B:
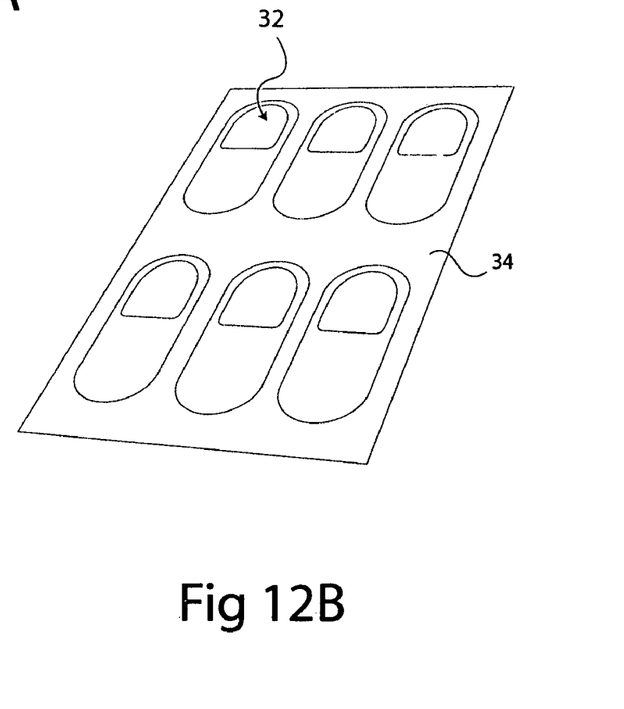
Figure 13A:
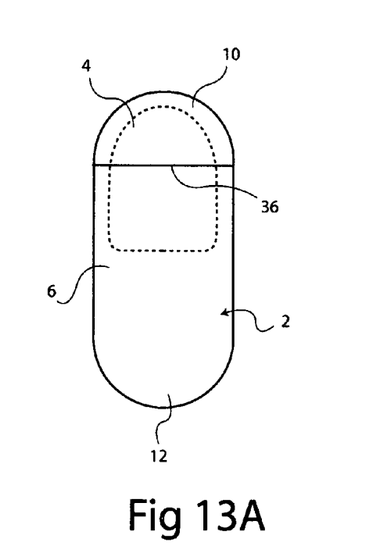
FIGS. 13A to 13B show a Direct Press On Veneer having an instrument engagement pocket.
Figure 13B:
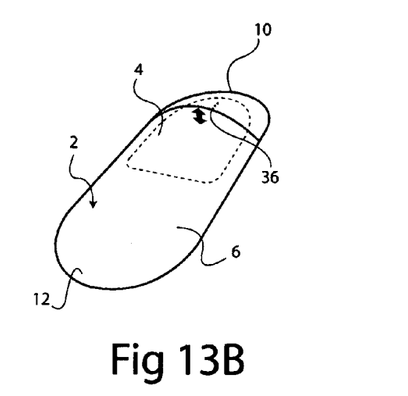
Figure 14:
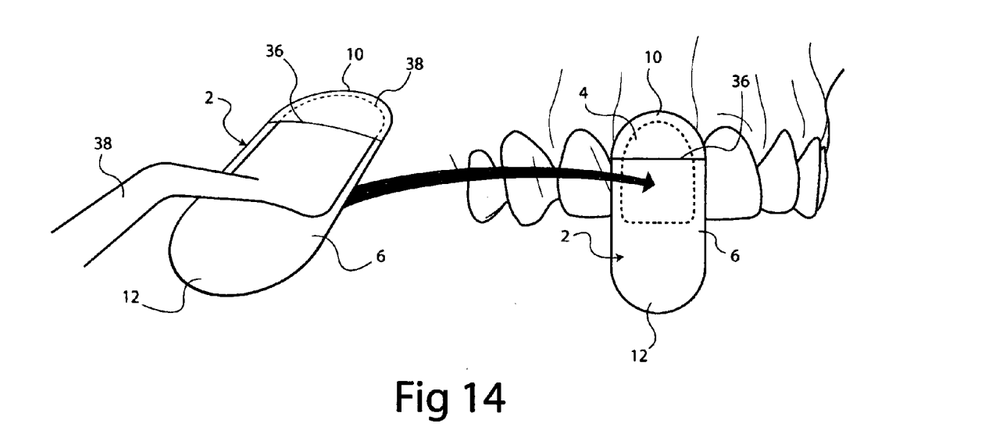
FIG. 14 shows an instrument engaging the pocket while applying the veneer to the tooth's surface.
Figure 15A:
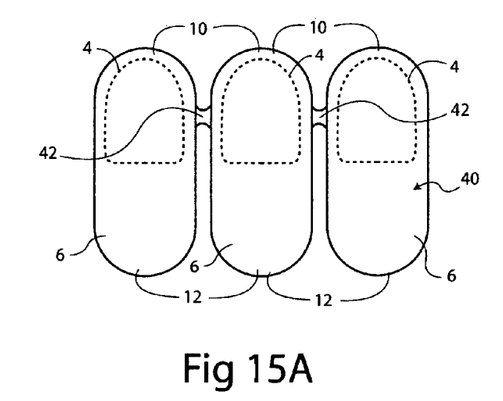
FIGS. 15A to 15B show a Press On Veneer with multiple interconnected veneers having accordion connections for simultaneous tooth applications.
Figure 15B:
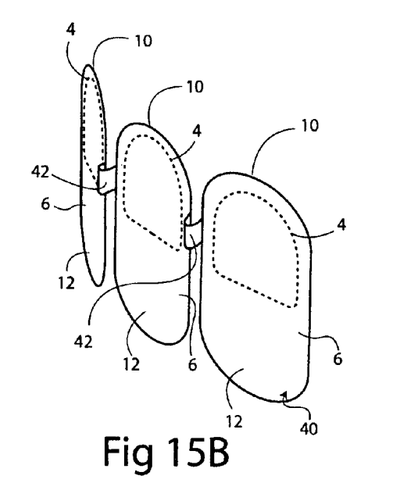
Figure 16:
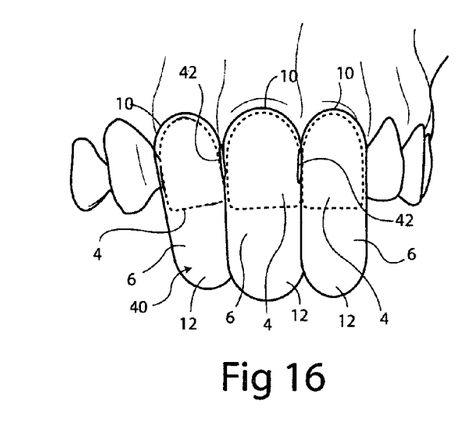
FIG. 16 shows a clinical representation of the multiple-connected veneers applied to corresponding tooth surfaces.
Figure 17A:
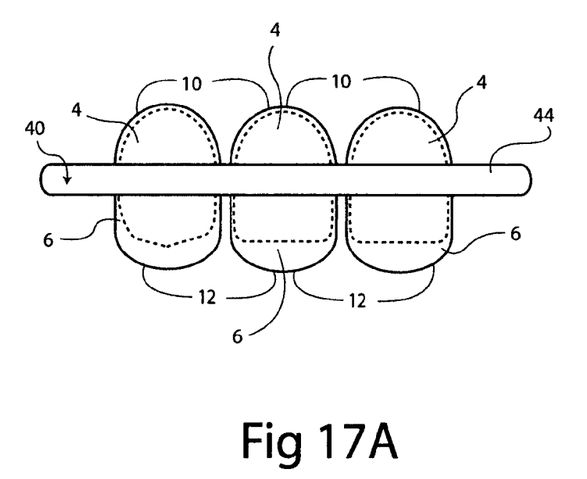
FIGS. 17A to 17B show multiple-connected Press On Veneers with an attached placing/peeling strip.
Figure 17B:
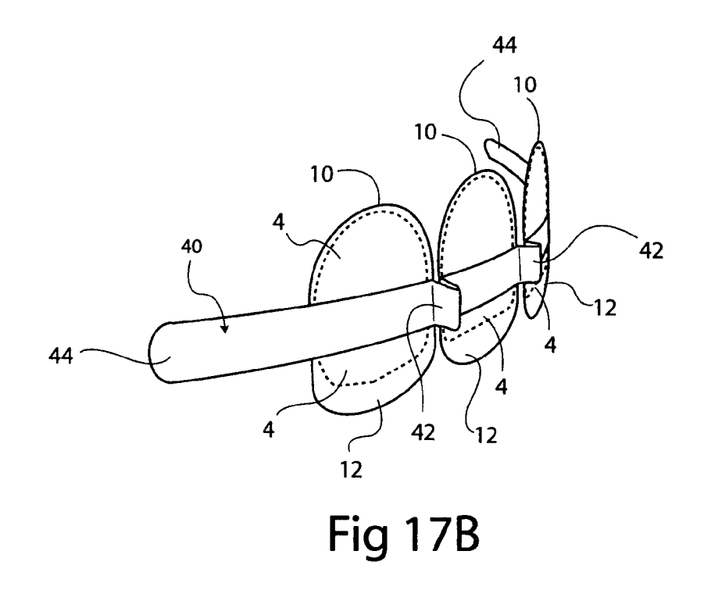

There are many possibilities with regard to the shape configuration and application of the direct resin veneer 2. These embodiments present a number of possibilities to improve the delivery of a resin veneer 4 to a tooth's surface as well as to provide for manufacturing alternatives. The direct press on veneer 2 illustrated in FIGS. 12A and 12B, for example, shows a press on veneer 2 with a single sided sheath design. The exposed resin veneer 4 portion is then applied in plural to a veneer card 34. FIGS. 13A and 13B shows an embodiment of a direct resin veneer 2 with the addition of a receptacle or instrument engaging pocket 36. This pocket 36 is designed to be interfaced with an appropriate engaging instrument 38 for a finger free resin veneer 4 placement on a tooth's surface FIG. 14. FIGS. 15A-15B shows a multiple-connected resin veneer 40 conjoined by two flexible joints or accordion connectors 42. These accordion connectors 42 are * designed to flex, allowing for customized veneer 40 spacing as determined by various patient tooth sizes. FIG. 16 shows how these flexible connections 42 permit a customized veneer 40 placement on multiple teeth. FIGS. 17A-17B shows a multiple-connected veneer 40 having a planar strip or accordion peel strip 44. The peel strip 44 is a singular length of material that interconnects the veneers 40 by their planar sheaths 6. Furthermore, the accordion peel strip 44 extends beyond the periphery of the veneers 40 to form a gripping area for grasping.

Operation—FIGS. 3-11

Figure 3:
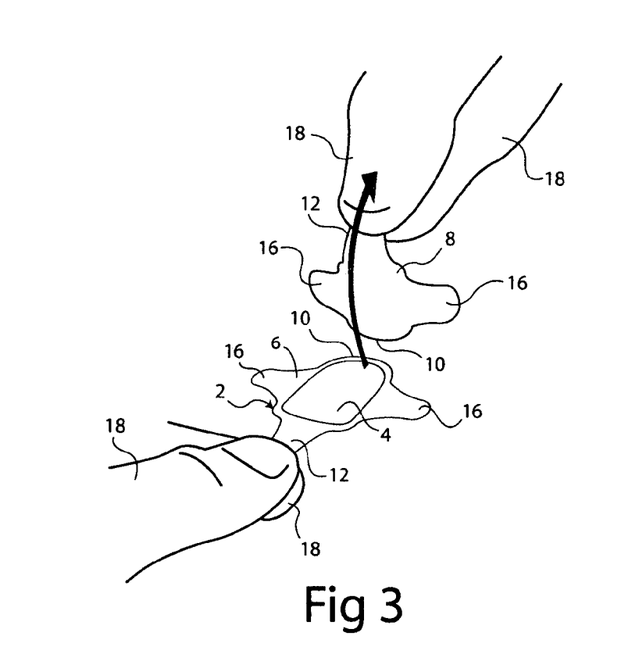
FIG. 3 shows an operator peeling apart the veneer's sheath halves.

The manner of using the direct press veneer 2 to restore a tooth's surface 20 relies on first exposing the resin veneer 4 for application. First, an operator 18 grasps the planar sheaths 6, 8 inferior peel tabs 12 and peels them apart (FIG. 3). The peeling tab separator 14 can serve to facilitate separation. By nature, the resin veneer 4 will remain adhered to the planar sheath 6 or the second planar sheath 8 only. After separation, the remaining sheath 6 or 8 may be discarded at this time (not shown). For this operation it is assumed that the secondary planar sheath 8 has been discarded.

Figure 5:
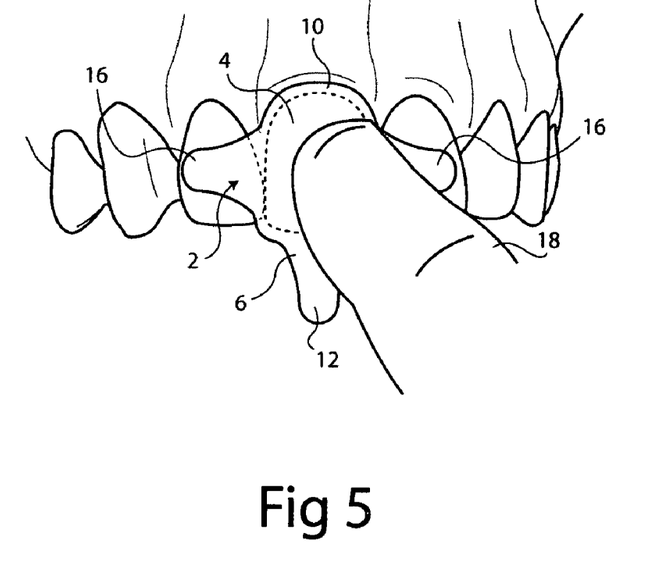
FIG. 5 shows an operator applying the press on veneer to the tooth's surface using gentle pressure.

Once separated, the operator 18 grips the planar sheath's lateral grasping tabs 16 and proceeds to transfer the exposed resin veneer 4 to the tooth surface 20 (FIG. 4). Prior to placement on the tooth surface 20, the operator 18 tangentially aligns the gingival arch contour 10 is with the gum. This will ensure that the resin veneers 4 superior apex will remain a short distance below the gum and prevent excessive intrusion during adaptation. After tangential alignment is achieved, the operator 18 uses gentle finger pressure against the planar sheath's 6 exterior to adhere the resin veneer 4 to the tooth surface 20 (FIG. 5).

Figure 6:
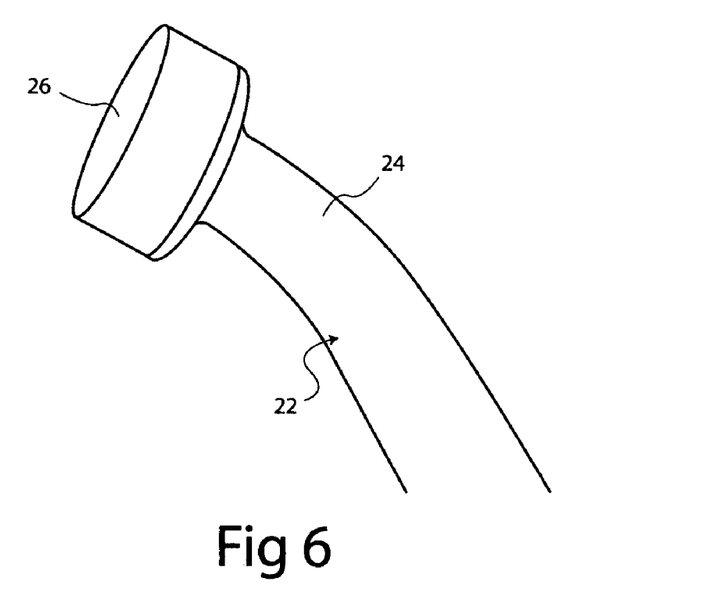
FIG. 6 shows a compressible foam applicator used to adapt the composite resin veneer to a tooth's surface.
Figure 7A:
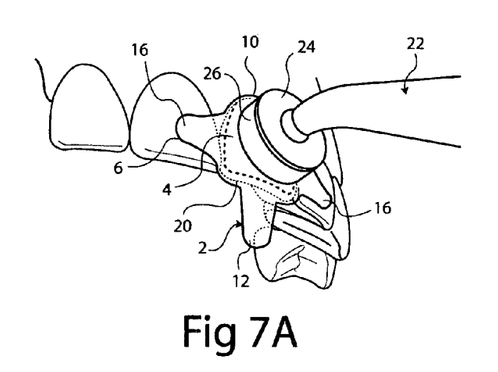
FIGS. 7A to 7C show various views of the compressible applicator compressively adapting the resin veneer through the sheath to the tooth's surface.

Now, the resin veneer 4 is ready for operative adaptation. To ensure proper adaptation, a soft compressible applicator 22 is used to adapt the veneer 4 through the planar sheath 6. Note, the compressible applicator 22 is comprised of an applicator body 24 for grasping and a compressible foam applicator 26 (FIG. 6). It is used to adapt the veneer 4 through the planar sheath 6. To begin adaptation, the foam applicator is placed against the sheath 6 (FIG. 7A).

Figure 7B:
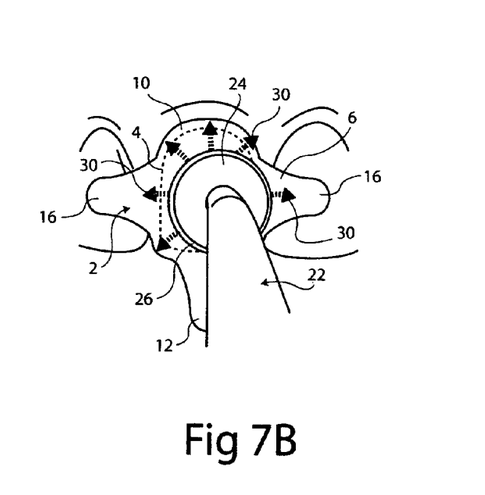
Figure 7C:
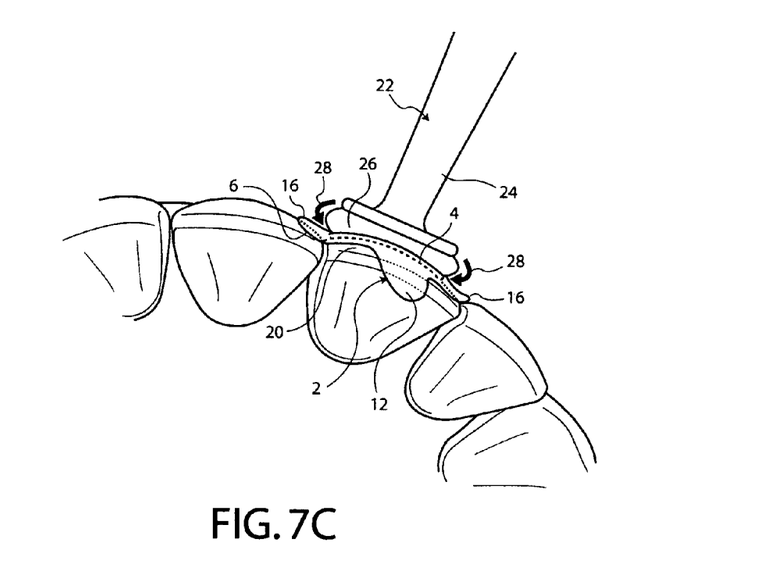

Next, the operator slides and compresses the foam applicator gently against the planar sheath 6 to create compressive forces 28 and sliding compressive forces 30. These forces 28, 30 adaptively conform the veneer 4 to the contours of the tooth's surface 20 (FIGS. 7B and 7C). Finally, once proper adaptation has been achieved, the operator 18 separates the planar sheath 6 from the resin veneer 4 by grasping and pulling on the inferior peeling tab 12 (FIG. 8) At this point, the veneer 4 remains affixed to the tooth surface 20. Note, the detached sheath 6 may then be discarded (not shown).

Figure 9A:
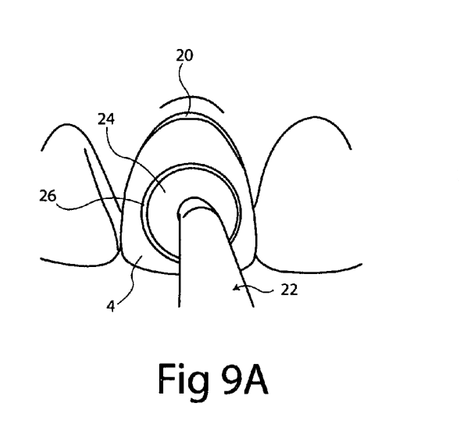
FIGS. 9A to 9B show the compressible applicator directly applied to the resin surface to smooth any inconsistencies.
Figure 9B:
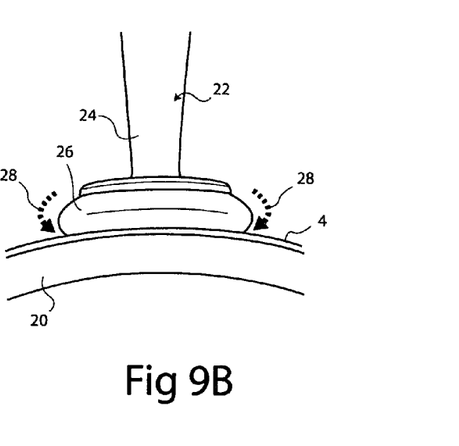
Figure 10:
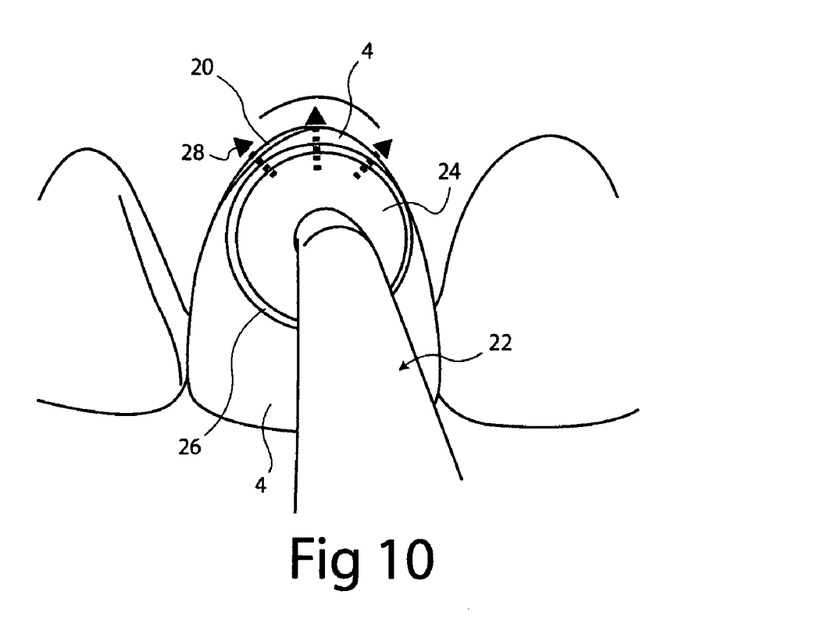
FIG. 10 shows the compressible applicator adapting the resin veneer into the gum line to cover any exposed tooth surface.
Figure 11:
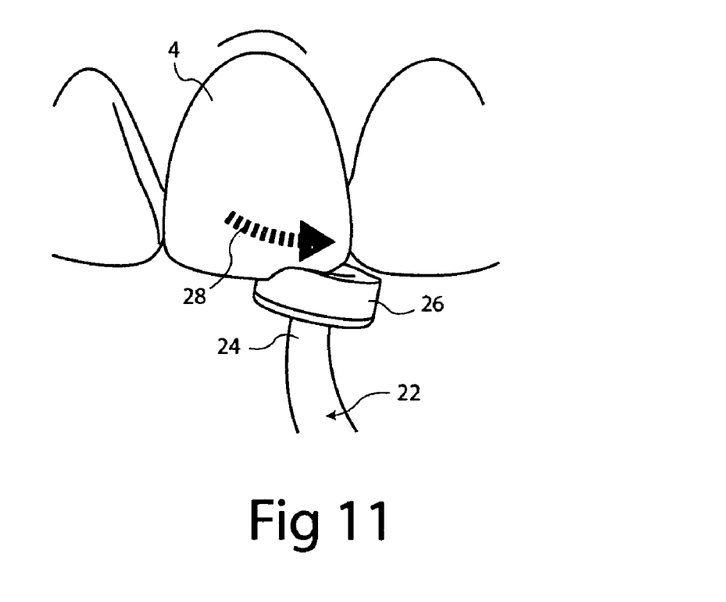
FIG. 11 shows the compressible applicator removing any excess resin from the tooth's incisal edge.

Next, the compressible applicator 22 is used to smooth any inconsistencies or impressions. This is accomplished by gently compressing the foam applicator 26 against the exposed resin veneers 4 surface (FIGS. 9A and 9B). Finally, the operator 18 adapts any remaining exposed tooth surface 20 near the gingival region (FIG. 10). This may be necessary due to incomplete resin veneer 4 adaptation resulting from the tangential alignment. Lastly, any excess resin veneer 4 may be compressively brushed from the tooth surface's 20 incisor edge using the compressible applicator 22 (FIG. 11).

Advantages

From the description above, a number of advantages of my direct resin veneer become evident:
(a) A full direct rein veneer can be rapidly placed without need for tedious incremental buildup
(b) Placement via a sheath ensures the resin surface will remain uncontaminated from debris
(c) The uniform initial thickness ensures a consistent appearance from tooth to tooth
(d) The ability to have very thin uniformly thin resin will ensure a very natural appearance.

Conclusion, Ramifications and Scope

Accordingly, the reader will see that the direct press on veneer can be used to create a superior finished veneer with vastly decreased time and effort. Additionally, the pre-formed thickness lends itself to a consistency not achievable with standard cosmetic techniques. The end result is a superior finish with substantial ease. The system also has vast implications for creating temporary veneers and splints for patients exhibiting periodontal disease. Furthermore, the direct resin veneer has additional advantages in that Permits predictable quality results from tooth to tooth
Allows for simultaneous multiple tooth veneers
Allows the clinician to achieve a quality result with systematic precision
Allows for controlled thickness for predictable multilayer veneers.

Although the description above contains much specificity, these should not be construed as to limiting the scope of the invention but merely as providing illustrations of some of the presently preferred embodiments of this invention. For example, the resin veneer may be of any size shape or thickness as to permit ideal results. If needed for optimal tooth splinting stability, fiber strands may be incorporated directly into the resin veneers. Any number of shades or restorative materials may be used. A multitude of shade and opacities may be combined into a single veneer to attain the appearance of more complex multi layer finishes.

Furthermore, the planar sheaths may be made from any material that optimally secures, delivers and separates from the resin veneer optimally. The pliability and flexibility of the sheath material also are variable to any degree to best operative adaptation. This may include proprietary materials not yet configured as well as commonly available non-stick materials and plastics. The sheath may be one sided or two sided and may be selectively sealed as needed to ensure resin freshness. Coatings or secondary emulsions may be added to its surface to improve its qualities. The sheath may be clear or opaque. Moreover the cover or sheath portions may have any configuration for optimal function. It may have any number of protrusions or extensions. Protrusions may also be eliminated.

Lastly, Additive gripping and peeling aids may be incorporated into the veneer cover or sheath to further enhance and facilitate usage. Examples could be strips of material or sticker additives to facilitate stability, placement and orientation and peeling functions.

Thus, the scope of the invention should be determined by the appended claims and their legal equivalents, rather than by the examples given.

I claim:

1. A method of placing a direct press on veneer comprising:
   (a) providing a precut layer of dental resin shaped in a configuration of a tooth surface and disposed between two flexible sheet covers, wherein the precut layer of dental resin is sized dimensionally slightly smaller than the tooth surface;
      wherein the precut layer of dental resin comprises a first side shaped convexly to correlate to a gingival side of the tooth, second and third sides shaped substantially straight and parallel to each other to correlate to lateral sides of the tooth and a fourth side shaped slightly convexly to correlate to an incisal side of the tooth;
      the flexible sheet covers comprising one or more extensions for removal of the flexible sheet covers from the dental resin, and further comprising a side shaped convexly to correlate with the first side of the precut layer of dental resin;
      wherein the precut layer of dental resin is adaptable to cover the entire tooth surface upon application to the tooth surface; and
      wherein one of the flexible covers comprises a pocket for insertion of a tool;
   (b) separating one flexible sheet cover from the precut layer of dental resin;
   (c) adhering the precut layer of dental resin to the tooth surface and tangentially aligning the convexly shaped side of the second flexible sheet cover with a gum line of the tooth;
   (e) removing the second flexible sheet from the precut layer of dental resin;
   (f) compressively adapting the precut layer of dental resin to the tooth surface; and
   (g) curing the adapted precut layer of dental resin.

2. The method of claim 1, wherein during the adhering step, the first side of the precut layer of dental resin is adhered proximate the gum line of the tooth surface.

3. The method of claim 2, wherein during the adhering step, the first side of the precut layer of dental resin is aligned a short distance below the gum line of the tooth surface.

4. Direct press on veneer comprising:
   a precut layer of dental resin shaped in a configuration of a tooth surface and disposed between two flexible sheet covers, wherein the precut layer of dental resin is sized dimensionally slightly smaller than the tooth surface;
   wherein the precut layer of dental resin comprises a first side shaped convexly to correlate to a gingival side of the tooth, second and third sides shaped substantially straight to correlate to lateral sides of the tooth and a fourth side shaped slightly convexly to correlate with an incisal side of the tooth;
   the flexible sheet covers comprising one or more extensions for removal of the flexible sheet covers from the precut layer of dental resin;
   wherein the precut layer of dental resin is adaptable to cover the entire tooth surface upon application to the tooth surface; and
   wherein one of the flexible covers comprises a pocket for insertion of a tool.

5. The direct press on veneer of claim 4, wherein the flexibleسheet covers comprise a side shaped convexly such that a substantially constant space is left between the entire perimeter of the first side of the resin and the convexly shaped side of the flexible sheet covers to correlate with the first side of the precut layer of dental resin.

6. The direct press on veneer of claim 5, wherein an extension of one of the flexible sheet covers comprises a tab at the end.

7. The direct press on veneer of claim 4, wherein the flexible covers are fabricated of a non-sticky material.

* * * * *